United States Patent
Shibata et al.

(10) Patent No.: US 9,580,604 B2
(45) Date of Patent: Feb. 28, 2017

(54) PENTAFLUOROSULFANYL PHTHALOCYANINE DERIVATIVES AND INTERMEDIATES THEREOF

(71) Applicants: UBE INDUSTRIES, LTD., Yamaguchi (JP); NAGOYA INSTITUTE OF TECHNOLOGY, Aichi (JP)

(72) Inventors: Norio Shibata, Aichi (JP); Norihito Iida, Aichi (JP); Etsuko Tokunaga, Aichi (JP); Norimichi Saito, New York, NY (US)

(73) Assignees: UBE INDUSTRIES, LTD. (JP); NAGOYA INSTITUTE OF TECHNOLOGY (JP)

( * ) Notice: Subject to any disclaimer, the term of this patent is extended or adjusted under 35 U.S.C. 154(b) by 0 days.

(21) Appl. No.: 14/648,202

(22) PCT Filed: Nov. 29, 2013

(86) PCT No.: PCT/JP2013/082136
§ 371 (c)(1),
(2) Date: May 28, 2015

(87) PCT Pub. No.: WO2014/084331
PCT Pub. Date: Jun. 5, 2014

(65) Prior Publication Data
US 2015/0337135 A1    Nov. 26, 2015

Related U.S. Application Data

(60) Provisional application No. 61/731,132, filed on Nov. 29, 2012.

(51) Int. Cl.
| | | |
|---|---|---|
| C07D 487/22 | (2006.01) | |
| C09B 47/04 | (2006.01) | |
| C07C 323/32 | (2006.01) | |
| C09B 47/067 | (2006.01) | |
| C07C 381/00 | (2006.01) | |

(52) U.S. Cl.
CPC .......... *C09B 47/04* (2013.01); *C07C 323/32* (2013.01); *C07C 381/00* (2013.01); *C07D 487/22* (2013.01); *C09B 47/0675* (2013.01)

(58) Field of Classification Search
CPC .................................................. C07D 487/22
See application file for complete search history.

*Primary Examiner* — Brian McDowell
(74) *Attorney, Agent, or Firm* — Swanson & Bratschun, L.L.C.

(57) ABSTRACT

Provided is a phthalocyanine derivative of the following general formula (1) which has superior solubility in organic solvents:
General formula (1):

[Formula 1]

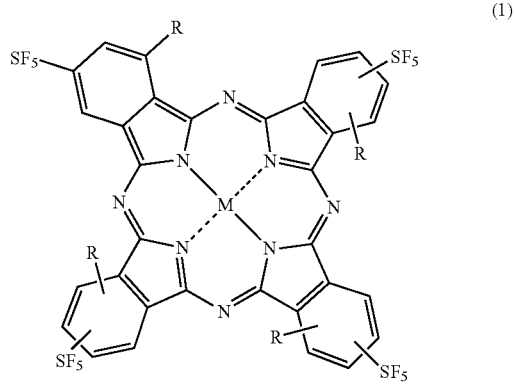

(1)

(wherein M is a hydrogen atom, a metal element, a metalloid element, a metal oxide, a metalloid oxide, a metal hydroxide, a metalloid hydroxide, a metal halide, or a metalloid halide, and R is each independently a hydrogen atom, an alkyl ethyl group, an aryl ether group, an alkyl sulfide group, an aryl sulfide group, or a trifluoromethyl group).

11 Claims, 5 Drawing Sheets

PENTAFLUOROSULFANYL PHTHALOCYANINE DERIVATIVES AND INTERMEDIATES THEREOF

RELATED APPLICATIONS

This application is a 35 U.S.C. §371 national phase application of International Application Serial No. PCT/JP2013/082136, filed Nov. 29, 2013 (WO 2014/084331). International Application Serial No. PCT/JP2013/082136 claims the benefit of U.S. Provisional Application Ser. No. 61/731,132, filed Nov. 29, 2012, which is incorporated herein by reference in its entirety.

TECHNICAL FIELD

The present invention relates to pentafluorosulfanyl phthalocyanine derivatives and intermediates thereof.

BACKGROUND ART

Phthalocyanines have been used as blue and green pigments. They are also functional dyes that have been used as charge generating agents and as dyes for magneto-optical disks due to their superior physical properties. Further, they are expected to be applied in various fields, including photosensitizers for photodynamic therapy and nonlinear optical materials. However, phthalocyanine derivatives generally have a problem in that they are poor in solubility in organic solvents. Thus, Patent Literature 1, and Non-patent Literatures 1 and 2 have reported phthalocyanines having trifluoromethyl groups introduced thereinto for the purpose of improving their solubility.

SUMMARY OF INVENTION

Technical Problem

As mentioned above, various attempts have been made to improve the solubility of phthalocyanines in organic solvents, but there is still no phthalocyanine that can achieve a sufficient level of solubility. In view of such circumstances, the present invention has as its object to provide phthalocyanine derivatives having superior solubility in organic solvents.

Solution to Problem

The present inventors have found that the above-mentioned object can be achieved by introducing, into a phthalocyanine, pentafluorosulfanyl groups which are fluorine-containing functional groups that are bulkier and more soluble than conventionally used trifluoromethyl groups, and thus have completed the present invention. More specifically, the above-mentioned object is achieved by the invention as follows.

[1] A phthalocyanine derivative of the following general formula (1):

[Formula 1]

(1)

(wherein M is a hydrogen atom, a metal element, a metalloid element, a metal oxide, a metalloid oxide, a metal hydroxide, a metalloid hydroxide, a metal halide, or a metalloid halide, and R is each independently a hydrogen atom, an alkyl ethyl group, an aryl ether group, an alkyl sulfide group, an aryl sulfide group, or a trifluoromethyl group).

[2] The phthalocyanine derivative as set forth in [1], wherein R is a hydrogen atom.

[3] The phthalocyanine derivative as set forth in [1], wherein R is an alkyl ethyl group, an aryl ether group, an alkyl sulfide group, an aryl sulfide group, or a trifluoromethyl group.

[4] The phthalocyanine derivative as set forth in [1], wherein R is a trifluoromethyl group, a phenoxy group, or a phenyl sulfide group.

[5] A halogen-containing pentafluorosulfanyl benzene derivative of the following general formula (2):

[Formula 2]

(2)

(wherein Hal is a halogen atom, and X is a hydrogen atom, a halogen atom, or a cyano group).

[6] A pentafluorosulfanyl phthalonitrile derivative of the following general formula (3):

[Formula 3]

(3)

(wherein R is a hydrogen atom, an alkyl ethyl group, an aryl ether group, an alkyl sulfide group, an aryl sulfide group, or a trifluoromethyl group).

[7] A process for preparing the phthalocyanine derivative as set forth in [1], the process comprising the steps of:

(A) providing a pentafluorosulfanyl phthalonitrile derivative of the following general formula (3):

[Formula 4]

(3)

(wherein R is a hydrogen atom, an alkyl ethyl group, an aryl ether group, an alkyl sulfide group, an aryl sulfide group, or a trifluoromethyl group); and (B) heating the pentafluorosulfanyl phthalonitrile derivative together with hydrogen, a metal, a metalloid, a metal oxide, a metalloid oxide, a metal hydroxide, a metalloid hydroxide, a metal halide, or a metalloid halide.

[8] The process as set forth in [7], wherein the step (A) is a step of providing the pentafluorosulfanyl phthalonitrile derivative of the general formula (3), by following a step of converting Hal and X in a halogen-containing pentafluorosulfanyl benzene derivative of the following general formula (2):

[Formula 5]

(2)

(wherein Hal is a halogen atom, and X is a hydrogen atom, a halogen atom, or a cyano group) into a cyano group and R, respectively.

[9] A process for preparing the phthalocyanine derivative as set forth in [2], the process comprising the steps of:

(A1) converting Hal in a halogen-containing pentafluorosulfanyl benzene derivative of the following general formula (2a):

[Formula 6]

(2a)

(wherein Hal is a halogen atom)

into a cyano group, to thereby provide a pentafluorosulfanyl phthalonitrile derivative of the following general formula (3a):

[Formula 7]

(3a)

and (B) heating the pentafluorosulfanyl phthalonitrile derivative together with hydrogen, a metal, a metalloid, a metal oxide, a metalloid oxide, a metal hydroxide, a metalloid hydroxide, a metal halide, or a metalloid halide.

[10] A process for preparing the phthalocyanine derivative as set forth in [3], the process comprising the steps of:

(A2) converting one Hal and the other Hal in a halogen-containing pentafluorosulfanyl benzene derivative of the following general formula (2b):

[Formula 8]

(2b)

(wherein Hal is a halogen atom)

into a cyano group and R', respectively, to thereby provide a pentafluorosulfanyl phthalonitrile derivative of the following general formula (3b):

[Formula 9]

(3b)

(wherein R' is an alkyl ether group, an aryl ether group, an alkyl sulfide group, an aryl sulfide group, or a trifluoromethyl group); and (B) heating the pentafluorosulfanyl phthalonitrile derivative together with hydrogen, a metal, a metalloid, a metal oxide, a metalloid oxide, a metal hydroxide, a metalloid hydroxide, a metal halide, or a metalloid halide.

[11] A process for preparing the phthalocyanine derivative as set forth in [3], the process comprising the steps of:

(A3) converting Hal in a halogen-containing pentafluorosulfanyl benzene derivative of the following general formula (2c):

[Formula 10]

(2c)

(wherein Hal is a halogen atom)
into R', to thereby provide a pentafluorosulfanyl phthalonitrile derivative of the following general formula (3c):

[Formula 11]

(3c)

(wherein R' is an alkyl ether group, an aryl ether group, an alkyl sulfide group, an aryl sulfide group, or a trifluoromethyl group); and (B) heating the pentafluorosulfanyl phthalonitrile derivative together with hydrogen, a metal, a metalloid, a metal oxide, a metalloid oxide, a metal hydroxide, a metalloid hydroxide, a metal halide, or a metalloid halide.

Advantageous Effects of Invention

The present invention can provide phthalocyanine derivatives having superior solubility in organic solvents.

DESCRIPTION OF EMBODIMENTS

Hereunder, the present invention will be described in detail. For the purpose of the invention, numerical ranges defined by their endpoints include the endpoints.

1. Phthalocyanine Derivatives

Phthalocyanines are cyclic compounds having a structure in which four phthalic imides are crosslinked by nitrogen atoms. As referred to in the present invention, the "phthalocyanine derivatives" refers to phthalocyanines or those having substituents introduced thereinto.

The phthalocyanine derivatives of the present invention are represented by the following general formula (1).

[Formula 12]

(1)

M is a hydrogen atom, a metal element, a metalloid element, a metal oxide, a metalloid oxide, a metal hydroxide, a metalloid hydroxide, a metal halide, or a metalloid halide.

The metal element refers to an alkali metal, an alkaline earth metal, a transition metal, a lanthanoid metal, or an actinoid metal. Specific examples include, but are not limited to, lithium, sodium, potassium, magnesium, calcium, scandium, yttrium, titanium, zirconium, chromium, manganese, molybdenum, iron, ruthenium, cobalt, rhodium, nickel, palladium, copper, zinc, aluminum, gallium, indium, tin, lanthanum, and uranium.

The metalloid element refers to an element having intermediate properties between those of metals and non-metals, and examples include, but are not limited to, boron, silicon, arsenic, germanium, and lead.

The metal oxide refers to an oxide of the metal element described above. Specific examples include, but are not limited to, lithium oxide, magnesium oxide, calcium oxide, titanium oxide, chromium oxide, manganese oxide, molybdenum oxide, iron oxide, ruthenium oxide, copper oxide, zinc oxide, aluminum oxide, gallium oxide, lanthanum oxide, and uranium oxide.

The metalloid oxide refers to an oxide of the metalloid element described above. Specific examples include, but are not limited to, boron oxide, silicon oxide, arsenic oxide, germanium oxide, and lead oxide.

The metal hydroxide refers to a hydroxide of the metal element described above. Specific examples include, but are not limited to, aluminum hydroxide, indium hydroxide and thallium hydroxide.

The metalloid hydroxide refers to a hydroxide of the metalloid element described above. Specific examples include, but are not limited to, boron hydroxide, silicon hydroxide, arsenic hydroxide, germanium hydroxide, and lead hydroxide.

The metal halide refers to a halide of the metal element described above, and the metalloid halide refers to a halide of the metalloid element described above. Specific examples include fluorides, chlorides, bromides, and iodides of these elements.

R is each independently a hydrogen atom, an alkyl ethyl group, an aryl ether group, an alkyl sulfide group, an aryl sulfide group, or a trifluoromethyl group. The alkyl group is not particularly limited as long as it does not impair the solubility of the phthalocyanine derivatives in organic solvents, but a straight or branched chain alkyl group having 1 to 5 carbon atoms is preferred. The aryl group is also not particularly limited as long as it does not impair the solubility of the phthalocyanine derivatives in organic solvents, but an aromatic group having 6 to 12 carbon atoms is preferred, and a phenyl group is more preferred. The aryl group may contain a branched or straight chain substituent having 1 to 3 carbon atoms.

Among the members of R, the alkyl ethyl group, aryl ether group, alkyl sulfide group, aryl sulfide group, or trifluoromethyl group may be designated as "R'".

Hereunder, some modes of the phthalocyanine derivatives of the present invention will be mentioned.

[Formula 13]

(1a)

(1b)

Preferred modes of the phthalocyanine derivative 1b are as follows.

[Formula 14]

1b-1

1b-2

1b-3

The phthalocyanine derivatives of the present invention not only have superior solubility in organic solvents, but also are hard to coagulate in solution and thus have solution stability. The organic solvents are not particularly limited, and examples include, but are not limited to: ether solvents such as diethyl ether, diisopropyl ether, n-butyl methyl ether, tert-butyl methyl ether, tetrahydrofuran, and dioxane; hydrocarbon solvents such as heptane, hexane, cyclopentane, and cyclohexane; halogenated hydrocarbon solvents such as chloroform, carbon tetrachloride, methylene chloride, dichloroethane, and trichloroethane; aromatic solvents such as benzene, toluene, xylene, cumene, cymene, mesitylene, diisopropylbenzene, pyridine, pyrimidine, pyrazine, and pyridazine; ester solvents such as ethyl acetate; ketone solvents such as acetone and methyl ethyl ketone; solvents like dimethyl sulfoxide and dimethylformamide; and alcoholic solvents such as methanol, ethanol, propanol, isopropyl alcohol, aminoethanol, and N,N-dimethylaminoethanol. Among them, N,N-dimethylaminoethanol is most preferred.

There are four types of structural isomers of the phthalocyanine derivatives of the present invention, and those isomers are also included by the phthalocyanine derivatives of this invention. In addition, the inventive phthalocyanine derivatives may form salts or may be present in the form of hydrates or solvates, and those salts, hydrates and solvates are also included by the inventive phthalocyanine derivatives.

The processes for preparing the phthalocyanine derivatives of the present invention will be described later.

2. Halogen-Containing Pentafluorosulfanyl Benzene Derivatives

The halogen-containing pentafluorosulfanyl benzene derivatives are represented by the following general formula (2).

[Formula 15]

(2)

Hal is a halogen atom. The halogen atom can be exemplified by a fluorine atom, a chlorine atom, a bromine atom, and an iodine atom, and from the viewpoint of ease of synthesis, a chlorine atom, a bromine atom, or an iodine atom is preferred, and an iodine atom is more preferred.

X is a hydrogen atom, a halogen atom, or a cyano group. The halogen atom as referred to in relation to X is also preferably a chlorine atom, a bromine atom, or an iodine atom, and more preferably an iodine atom, as described above. If X is a halogen atom, the halogen atom need not always be of the same type as Hal.

As described later, the halogen-containing pentafluorosulfanyl benzene derivatives of the present invention (hereinafter also briefly referred to as the "halogen-containing derivatives") are useful as a starting material for preparing the phthalocyanine derivatives of this invention. Those modes of the halogen-containing derivatives which are preferred from this viewpoint are as follows.

[Formula 16]

The halogen-containing derivatives 2a and 2b are obtained by reacting pentafluorosulfanyl cyanobenzene with a halogen source in the presence of alkyllithium (refer to Non-patent Literature 3). The halogen-containing derivative 2b is further reacted with a cyanide to thereby obtain the halogen-containing derivative 2c. The reaction scheme is shown below.

[Formula 17]

Examples of the organic lithium compound that can be used in this reaction include n-butyllithium, sec-butyllithium, tert-butyllithium, lithium diisopropylamide, lithium bistrimethylsilylamide, and lithium 2,2,6,6-tetramethylpiperidide, with lithium 2,2,6,6-tetramethylpipmidide being preferred from the viewpoint of reactivity. As the halogen source, molecular halogen, N-halogen succinimide, or N-halogen saccharin can be used. From the viewpoint of reactivity, the halogen source is preferably a molecular halogen such as $Cl_2$, $I_2$, or $Br_2$, and more preferably $I_2$.

The halogen-containing derivative 2a or 2b can be selectively synthesized depending on the amount of the halogen source to be used. More specifically, when the halogen source is used in excessive amounts, the halogen-containing derivative 2b can be synthesized.

Examples of the solvent that can be used in this reaction include ethers such as tetrahydrofuran and diethyl ether, with tetrahydrofuran being particularly preferred from the viewpoint of ease of handling, etc. The reaction temperature can be set to be in the range of −20° C. to −78° C., and is preferably on the order of −78° C.

In respect of the reaction of the halogen-containing derivative 2b with a cyanide, the cyanide that can be used in this reaction is not particularly limited, and examples include, but are not limited to, sodium cyanide, potassium cyanide, copper cyanide, zinc cyanide, and trimethylsilyl cyanide, with copper cyanide being preferred from the viewpoint of reactivity. Examples of the solvent that can be used in this reaction include dimethylformamide, dimethyl sulfoxide, and N-methylpyrrolidone, with dimethylformamide being preferred from the viewpoint of ease of handling, etc. This reaction can be conducted at a temperature from 0°

C. to the boiling point of the solvent used, and is preferably conducted at a temperature of 50 to 200° C.

3. Pentafluorosulfanyl Phthalonitrile Derivatives

Pentafluorosulfanyl phthalonitrile is a compound in which a $SF_5$ group is introduced into phthalonitrile. For the purpose of the present invention, the pentafluorosulfanyl phthalonitrile derivatives refer to pentafluorosulfanyl phthalonitrile, or compounds in which any other group besides $SF_5$ group is introduced into said compound, and are represented by the following general formula (3). The pentafluorosulfanyl phthalonitrile derivatives of this invention are hereinafter also briefly referred to as the "phthalonitrile derivatives".

[Formula 18]

(3)

R is a hydrogen atom, an alkyl ethyl group, an aryl ether group, an alkyl sulfide group, an aryl sulfide group, or a trifluoromethyl group. The alkyl and aryl groups have been described earlier in relation to the phthalocyanine derivatives. Specific modes of the phthalonitrile derivatives are shown below.

[Formula 19]

(3a)

(3b)

R' is an alkyl ether group, an aryl ether group, an alkyl sulfide group, an aryl sulfide group, or a trifluoromethyl group.

As discussed later, the phthalonitrile derivatives of the present invention are useful as a starting material for preparing the phthalocyanine derivatives of this invention. Those modes of the phthalonitrile derivative 3b which are preferred from this viewpoint are as follows.

[Formula 20]

(3b-1)

(3b-2)

(3b-3)

In these formulas, Rb is a straight or branched chain alkyl group having 1 to 3 carbon atoms. The symbol n represents the number of Rb's, and is an integer ranging from 0 to 5. Since there may occur a decrease in reactivity in the presence of excessive amounts of Rb, n is preferably in the range of 0 to 2, more preferably 0 or 1, and much more preferably 0. Likewise, since there may also occur a decrease in reactivity when Rb is bulky, Rb, if present, is preferably a methyl group.

The phthalonitrile derivative 3a is obtained by reacting the halogen-containing derivative 2a mentioned above with a cyanide. The reaction conditions and other factors are as described earlier in the section regarding the halogen-containing derivatives.

The phthalonitrile derivative 3b can be obtained by converting the halogen atom in the aforesaid halogen-containing derivative 2c into R'. For example, when the halogen-containing derivative is reacted with a Yagupolskii's reagent, the phthalonitrile derivative 3b-1 (refer to Non-patent Literature 4) can be prepared; when it is reacted with a phenol, the phthalonitrile derivative 3b-2 (refer to Non-patent Literature 5) can be prepared; and when it is reacted with a thiophenol, the phthalonitrile derivative 3b-3 (refer to Non-patent Literature 6) can be prepared.

4. Process for Preparing the Phthalocyanine Derivatives

The phthalocyanine derivatives of the present invention can be prepared by a process comprising the steps of:

(A) providing a phthalonitrile derivative of the general formula (3); and

(B) heating the pentafluorosulfanyl phthalonitrile derivative together with hydrogen, a metal, a metalloid, a metal oxide, a metalloid oxide, a metal hydroxide, a metalloid hydroxide, a metal halide, or a metalloid halide.

The reaction scheme is shown below.

[Formula 21]

-continued (1) Step (A)

At this step, a phthalonitrile derivative of the general formula (3) is provided as described earlier.

(2) Step (B)

At this step, the phthalonitrile derivative of the general formula (3) is heated together with hydrogen, a metal, a metalloid, a metal oxide, a metalloid oxide, a metal hydroxide, a metalloid hydroxide, a metal halide, or a metalloid halide, to thereby obtain a phthalocyanine derivative of the general formula (1).

For convenience sake, hydrogen, a metal, a metalloid, a metal oxide, a metalloid oxide, a metal hydroxide, a metalloid hydroxide, a metal halide, or a metalloid halide is also referred to as a "core component".

The reaction conditions to be used at this step can be any conditions that are commonly adopted to prepare phthalocyanine. For example, the molar ratio of the phthalonitrile derivative of the general formula (3) to a core component can be any ratio within the range of 3:1 to 5:1. The heating temperature is preferably in the range of 180 to 250° C.

From the viewpoint of ease of preparation, it is preferred that this reaction be conducted in a sealed tube under solvent-free conditions, but the reaction may also be performed in a solvent. The solvent that can be used is not limited, and examples include: ether solvents such as diethyl ether, diisopropyl ether, n-butyl methyl ether, tert-butyl methyl ether, tetrahydrofuran, and dioxane; hydrocarbon solvents such as heptane, hexane, cyclopentane, and cyclohexane; halogenated hydrocarbon solvents such as chloroform, carbon tetrachloride, methylene chloride, dichloroethane, and trichloroethane; aromatic solvents such as benzene, toluene, xylene, cumene, cymene, mesitylene, diisopropylbenzene, pyridine, pyrimidine, pyrazine, and pyridazine; ester solvents such as ethyl acetate; ketone solvents such as acetone and methyl ethyl ketone; solvents like dimethyl sulfoxide and dimethylformamide; alcoholic solvents such as methanol, ethanol, propanol, isopropyl alcohol, aminoethanol, and N,N-dimethylaminoethanol; supercritical carbon dioxide; and ionic liquids.

EXAMPLES

Example 1

Synthesis of 2-iodo-4-pentafluorosulfanyl cyanobenzene

[Formula 22]

A 30 mL three-neck flask purged with nitrogen was charged with 0.15 mL (0.87 mmol) of 2,2-6,6-tetramethylpiperidine (produced by Aldrich) and 2.0 mL of THF (produced by Kanto Chemical Co., Inc.), and then cooled to 0° C. To the mixture, 0.60 mL (1.5 M, 0.87 mmol) of n-BuLi (produced by Mitsuwa Chemicals Co., Ltd.) was added dropwise slowly, and the reaction was stirred at 0° C. for 30 minutes. The reaction solution was cooled to −78° C., and a solution obtained by dissolving, in 2.0 mL of THF, 100 mg (0.44 mmol) of 4-pentafluorosulfanyl cyanobenzene which had been synthesized by a procedure described below was added dropwise slowly. After stirring at −78° C. for one hour, 2.0 mL of a solution of 122 mg (0.87 mmol) of iodine (produced by Nacalai Tesque, Inc.) in THF was added dropwise slowly, and the mixture was stirred at −78° C. for 2 hours. Thereafter, the mixture was warmed to room temperature and stirred at room temperature for one hour, and then 3.0 mL of water was added to quench the reaction. The reaction solution was concentrated and then subjected to extraction with diethyl ether three times. The organic phase was washed with each of an aqueous 1N HCl solution, an aqueous sodium thiosulfate solution, and saturated saline in this order, and then dried over sodium sulfate. After concentration, the concentrate was purified by silica-gel column chromatography (Hex/AcOEt=95/5), whereby 60 mg of the product of interest was obtained (with a yield of 38%).
$^1$H NMR (300 MHz, CDCl$_3$): δ=7.73 (d, J=8.4 Hz, 1H), 7.87 (dd, J=8.4 Hz, J=1.5 Hz, 1H), 8.29 (d, J=1.5 Hz, 1H)
$^{19}$F NMR (282 MHz, CDCl$_3$): δ=−150.0 (quintet, J=150.6 Hz, 1F), −168.1 (d, J=150.6 Hz, 4F)

Synthesis of 4-pentafluorosulfanyl cyanobenzene

There was provided a 500 mL flask equipped with a condenser tube, a CaCl$_2$ tube, and a stirrer. The flask was charged with 73.4 g (0.33 mol) of 1-fluoro-4-pentafluorosulfanyl benzene (produced by UBE America Inc.), 32.5 g (0.66 mol) of NaCN (produced by Sigma-Aldrich) and 300 mL of dry DMSO (produced by Sigma-Aldrich). After the temperature in the flask was increased to the range of 100 to 105° C., the flask was heated for a total of 47 hours. GC analysis showed that the conversion achieved was about 75%.

The reaction mixture was deactivated with excessive amounts of water and subjected to extraction with CH$_2$Cl$_2$. After the CH$_2$Cl$_2$ phase was concentrated, the residues were dissolved in a Hex(hexane)/CH$_2$Cl$_2$ liquid mixture, and the solution was dried over Na$_2$SO$_4$. After filtration, the filtrate was concentrated to give 61.0 g of a yellow crude product.

The crude product was dissolved in a minimum volume of methanol at room temperature and then dried under vacuum. The resulting final product was a white crystal with a yield of 36.14 g and a purity of 95% as determined by GC analysis. MS and NMR analyses confirmed that the final product was 4-pentafluorosulfanyl cyanobenzene.

Example 2

Synthesis of 4-pentafluorosulfanyl phthalonitrile

[Formula 23]

A 30 mL eggplant flask purged with nitrogen was charged with 200 mg (0.56 mmol) of the 2-iodo-4-pentafluorosulfanyl cyanobenzene obtained in Example 1 and 151 mg (1.7 mmol) of copper cyanide (produced by Kishida Chemical Co., Ltd.). Further, 5.0 mL of dimethylformamide (produced by Kanto Chemical Co., Inc.) was added to allow it to dissolve the starting materials. The solution was heated to 110° C. and stirred for 5 hours. Then, after the solution was cooled to room temperature, saturated ammonia water was added and the mixture was subjected to extraction with diethyl ether. The organic phase was washed with each of saturated ammonia chloride water and saturated saline in this order, and then dried over sodium sulfate. After the organic phase was concentrated, the concentrate was purified by silica-gel column chromatography (Hex/AcOEt=9/1), whereby 62 mg of the product of interest was obtained (with a yield of 43%).

$^1$H NMR (300 MHz, CDCl$_3$): δ=7.98 (d, J=8.7 Hz, 1H), 8.15 (d, J=8.7 Hz, 1H), 8.20 (s, 1H)

$^{19}$F NMR (282 MHz, CDCl$_3$): δ=−151.6 (quintet, J=151.4 Hz, 1F), −168.1 (d, J=151.4 Hz, 4F)

Example 3

Synthesis of 2,6-diiodo-4-pentafluorosulfanyl cyanobenzene

[Formula 24]

A 100 mL eggplant flask purged with nitrogen was charged with 1.47 mL (8.73 mmol) of 2,2-6,6-tetramethyl-piperidine and 10 mL of THF, and then cooled to 0° C. To the mixture, 6.42 mL (1.36 M, 8.73 mmol) of n-BuLi was added dropwise slowly, and the reaction was stirred at 0° C. for 30 minutes. The reaction solution was cooled to −78° C., and a solution obtained by dissolving 500 mg (2.18 mmol) of 4-pentafluorosulfanyl cyanobenzene in 5.0 mL of THF was added dropwise slowly. After stirring at −78° C. for one hour, 5.0 mL of a solution of 2.43 mg (9.60 mmol) of iodine in THF was added dropwise slowly, and the mixture was stirred at −78° C. for 2 hours. Thereafter, the mixture was warmed to room temperature and stirred at room temperature for one hour, and then 6.0 mL of water was added to quench the reaction. The reaction solution was concentrated and then subjected to extraction with ethyl acetate three times. The organic phase was washed with each of an aqueous 1N HCl solution, an aqueous sodium thiosulfate solution, and saturated saline in this order, and then dried over sodium sulfate. After concentration, the concentrate was purified by silica-gel column chromatography (Hex/AcOEt=95/5), whereby 840 mg of the product of interest was obtained (with a yield of 80%).

$^1$H NMR (300 MHz, CDCl$_3$): δ=8.24 (s, 2H)

$^{19}$F NMR (282 MHz, CDCl$_3$): δ=−150.8 (quintet, J=160.4 Hz, 1F), −167.7 (d, J=160.4 Hz, 4F)

Example 4

Synthesis of 3-iodo-5-pentafluorosulfanyl phthalonitrile

[Formula 25]

A 50 mL eggplant flask purged with nitrogen was charged with 500 mg (1.04 mmol) of the 2,6-diiodo-4-pentafluorosulfanyl cyanobenzene obtained in Example 3 and 140 mg (1.56 mmol) of copper cyanide. Further, 10.0 mL of dimethylformamide (produced by Kanto Chemical Co., Inc.) was added to allow it to dissolve the starting materials. The solution was heated to 110° C. and stirred for 5 hours. Then, after the solution was cooled to room temperature, saturated ammonia water was added and the mixture was subjected to extraction with ethyl acetate. The organic phase was washed with each of saturated ammonia chloride water and saturated saline in this order, and then dried over sodium sulfate. After the organic phase was concentrated, the concentrate was purified by silica-gel column chromatography (Hex/AcOEt=9/1), whereby 87 mg of the product of interest was obtained (with a yield of 22%).

$^1$H NMR (300 MHz, CDCl$_3$): δ=8.17 (d, J=1.65 Hz, 1H), 8.50 (d, J=1.65 Hz, 1H)

$^{19}$F NMR (282 MHz, CDCl$_3$): δ=−152.27 (quintet, J=159 Hz, 1F), −167.72 (d, J=159 Hz, 4F)

Example 5

Synthesis of 3-trifluoromethyl-5-pentafluorosulfanyl phthalonitrile

[Formula 26]

A test tube purged with argon was charged with 50 mg (0.132 mmol) of the 3-iodo-5-pentafluorosulfanyl phthalonitrile obtained in Example 4, 106 mg (0.263 mmol) of a Yagupolskii's reagent which had been synthesized by a procedure described below, and 25 mg (0.395 mmol) of copper (produced by Nacalai Tesque, Inc.). Further, 1.0 mL of N,N-dimethylformamide was added to allow it to dissolve the starting materials. The solution was heated and stirred at 60° C. overnight. After completion of the reaction, the solution was cooled to room temperature, water was added, and the mixture was subjected to extraction with ethyl acetate. The organic phase was washed with saturated saline, and dried over sodium sulfate. The crude product obtained by concentration was purified by silica-gel column chromatography (Hex/AcOEt=9/1), whereby 35 mg of the product of interest was obtained (with a yield of 83%).

$^1$H NMR (300 MHz, CDCl$_3$): δ=8.38 (s, 1H), 8.39 (s, 1H)

$^{19}$F NMR (282 MHz, CDCl$_3$): δ=−62.73 (s, 3F), −153.2 (quintet, J=161.8 Hz, 1F), −167.8 (d, J=161.8 Hz, 4F)

<Procedure for Synthesizing a Yagupolskii's Reagent>

A Yagupolskii's reagent was synthesized in two stages as described below.

[Formula 27]

(1st stage)

A 100 mL eggplant flask purged with argon was charged with 4.5 g (29 mmol) of sodium trifluoromethyl sulfonate, and 15.4 mL (174 mmol) of trifluoromethanesulfonic acid was added dropwise slowly. After the mixture was stirred at room temperature for 5 minutes, 3.9 mL (43.5 mmol) of benzene was added dropwise slowly, and the mixture was stirred at 60° C. for 3 hours. After completion of the reaction, the reaction solution was cooled to 0° C., water was added slowly to quench the reaction, and then the solution was subjected to extraction with methylene chloride three times. The organic phase was washed with saturated saline, and dried over sodium sulfate. The crude product obtained by distilling off the solvent under reduced pressure was purified by silica-gel column chromatography (Hex/AcOEt=9/1), whereby 4.6 g of the product of interest was obtained (with a yield of 81%).

[Formula 28]

(2nd stage)

Yagupolskii's reagent

A 300 mL eggplant flask purged with nitrogen was charged with 4.5 g (23.1 mmol) of the source product synthesized in the first stage and 61.7 mL (695 mmol) of benzene, and then cooled to 0° C. 19 mL (116 mmol) of trifluoromethanesulfonic anhydride was added dropwise slowly, and the reaction was stirred at 0° C. for one hour. After completion of the reaction, water was added slowly to quench the reaction, and then the solution was subjected to extraction with methylene chloride three times. The organic phase was washed with saturated saline, and dried over sodium sulfate. The crude product obtained by distilling off the solvent under reduced pressure was recrystallized with a mixed solvent (hexane/ethyl acetate=8/2) to give 5.0 g of a Yagupolskii's reagent (with a yield of 54%).

$^1$H NMR (300 MHz, CD$_3$COCD$_3$): d 8.43 (d, J=8.1 Hz, 2H), 8.13 (t, J=7.5 Hz, 1H), 8.00 (t, J=8.1 Hz, 2H).

$^{19}$F NMR (282 MHz, CD$_3$COCD$_3$): d −51.0 (s, 3F), −78.5 (s, 3F).

Example 6

Synthesis of 3-phenoxy-5-pentafluorosulfanyl phthalonitrile

[Formula 29]

A test tube purged with argon was charged with 38 mg (0.10 mmol) of the 3-iodo-5-pentafluorosulfanyl phthalonitrile obtained in Example 4, 10.4 mg (0.11 mmol) of phenol (produced by Aldrich), and 48.9 mg (0.15 mmol) of cesium carbonate (produced by Kishida Chemical Co., Ltd.). Further, 1.0 mL of N-methylpyrrolidone (produced by Aldrich)

was added to allow it to dissolve the starting materials, and the solution was stirred at room temperature. After the stirring for one hour, water was added and the mixture was subjected to extraction with diethyl ether three times. The organic phase was washed with saturated saline, and then dried over sodium sulfate. The crude product obtained by concentrating the organic phase was purified by silica-gel column chromatography (Hex/AcOEt=9/1), whereby 28 mg of the product of interest was obtained (with a yield of 81%).

$^1$H NMR (300 MHz, CDCl$_3$): δ=7.14 (d, J=8.1 Hz, 2H), 7.36-7.41 (m, 2H), 7.51 (d, J=8.4 Hz, 1H), 7.55 (d, J=2.0 Hz, 1H), 7.81 (d, J=2.0 Hz, 1H)

$^{19}$F NMR (282 MHz, CDCl$_3$): δ=−151.7 (quintet, J=150.8 Hz, 1F), −168.3 (d, J=150.8 Hz, 4F)

Example 7

Synthesis of 3-thiophenoxy-5-pentafluorosulfanyl phthalonitrile

[Formula 30]

A 10 mL eggplant flask purged with argon was charged with 80 mg (0.21 mmol) of the 3-iodo-5-pentafluorosulfanyl phthalonitrile obtained in Example 4, 24 mg (0.23 mmol) of potassium carbonate (produced by Nacalai Tesque, Inc.), 2.0 mg (5 mol %) of copper iodide (produced by Wako Pure Chemical Industries, Ltd.), and 2.0 mL of isopropanol (produced by Wako Pure Chemical Industries, Ltd.), and then degassed with argon three times. 24 µL (0.42 mmol) of ethylene glycol (produced by Nacalai Tesque, Inc.) and 24 µL (0.23 mmol) of thiophenol (produced by Tokyo Chemical Industry Co., Ltd.) were added, and the mixture was stirred at room temperature. After the stirring for 3 hours, water was added and the solution was subjected to extraction with diethyl ether three times. The organic phase was washed with each of a 1 M aqueous sodium hydroxide solution and saturated saline, and dried with sodium sulfate. The concentrated crude product was purified by silica-gel column chromatography (Hex/AcOEt=9/1), whereby 56 mg of the product of interest was obtained (with a yield of 74%).

$^1$H NMR (300 MHz, CDCl$_3$): δ=7.36 (d, J=1.4 Hz, 1H), 7.52-7.61 (m, 5H), 7.82 (d, J=1.4 Hz, 1H)

$^{19}$F NMR (282 MHz, CDCl$_3$): δ=−151.6 (quintet, J=151.8 Hz, 1F), −168.5 (d, J=150.6 Hz, 4F)

Example 8

Synthesis of tetrakis(pentafluorosulfanyl)zinc phthalocyanine

[Formula 31]

M = ZnCl$_2$

A 10 mL eggplant flask purged with nitrogen was charged with 51 mg (0.20 mmol) of the 4-pentafluorosulfanyl phthalonitrile obtained in Example 2 and 9.1 mg (0.066 mmol) of zinc chloride (produced by Nacalai Tesque, Inc.). Further, N,N-dimethylaminoethanol (produced by Tokyo Chemical Industry Co., Ltd.) was added to allow it to dissolve the starting materials, and the solution was heated to 140° C. and stirred overnight. After the solution was cooled to room temperature, a 1 M aqueous hydrochloric acid solution was added to filter out the precipitated crystals, which were then washed with each of water, diethyl ether, and hexane in this order. The crystals were dried under reduced pressure in a desiccator, and then purified by silica-gel column chromatography (Hex/AcOEt=7/3), whereby 5.2 mg of the product of interest was obtained (with a yield of 10%).

$^1$H NMR (300 MHz, CDCl$_3$): δ=asymmetric form: 8.40 to 9.42 (m, 3H), symmetric form: 8.10 (d, J=8.4 Hz, 1H), 8.25 (s, 1H), 8.39 (d, J=8.4 Hz, 1H)

$^{19}$F NMR (282 MHz, d-acetone): δ=asymmetric form: −144.3 (quintet, J=147.9 Hz, 1F), −164.3 (d, J=147.9 Hz, 4F), symmetric form: −147.2 (quintet, J=149.5 Hz, 1F), −166.5 (d, J=149.5 Hz, 4F)

MALDI-TOF calculated for C$_{32}$H$_{12}$F$_{20}$N$_8$S$_4$Zn [M-H$^+$]$^-$ 1079.9. found 1082.11.

Example 9

Synthesis of α-tetrakis(trifluoromethyl)-β-tetrakis(pentafluorosulfanyl)zinc phthalocyanine

[Formula 32]

M = ZnCl$_2$

An ampoule tube purged with nitrogen was charged with 27 mg (0.0826 mmol) of the 3-trifluoromethyl-5-pentafluorosulfanyl phthalonitrile obtained in Example 5 and 3.8 mg (0.0275 mmol) of zinc chloride, and sealed and heated at 230° C. After the heating for 5 hours, the solution was cooled to room temperature and purified by silica-gel column chromatography (Hex/AcOEt=8/2), whereby 3.8 mg of the product of interest was obtained (with a yield of 10%).

$^1$H NMR (300 MHz, CDCl$_3$): δ=8.83 to 8.87 (m, 4H), 9.81 to 10.15 (m, 4H)

$^{19}$F NMR (282 MHz, d-acetone): δ=−59.22 to −61.68 (m, 12F), −146.65 to −147.81 (m, 4F), −164.52 to −166.71 (m, 16F)

MALDI-TOF calculated for $C_{36}H_8F_{32}N_8S_4Zn$ [M-H$^+$]$^−$ 1354.1. found 1352.05.

Example 10

Synthesis of α-tetrakis(phenoxy)-β-tetrakis(pentafluorosulfanyl)zinc phthalocyanine

[Formula 33]

M = ZnCl$_2$

An ampoule tube purged with argon was charged with 24 mg (0.069 mmol) of the 3-phenoxy-5-pentafluorosulfanyl phthalonitrile obtained in Example 6 and 3.1 mg (0.023 mmol) of zinc chloride, and sealed and heated to 220° C. After the heating for 4 hours, the solution was cooled to room temperature and purified by silica-gel column chromatography (Benzene/AcOEt=9/1), whereby 4.7 mg of the product of interest was obtained (with a yield of 14%).

$^1$H NMR (300 MHz, CDCl$_3$): δ=7.01 to 7.47 (m, 20H), 7.54 to 9.70 (m, 8H)

$^{19}$F NMR (282 MHz, CDCl$_3$): δ=−144.3 to −145.9 (m, 4F), −163.8 to −165.0 (m, 20F)

MALDI-TOF calculated for $C_{56}H_{28}F_{20}N_8O_4S_4Zn$ [M-H$^+$]$^−$ 1448.01. found 1447.88.

Example 11

Synthesis of α-tetrakis(thiophenoxy)-β-tetrakis(pentafluorosulfanyl)zinc phthalocyanine

[Formula 34]

M = ZnCl$_2$

An ampoule tube purged with argon was charged with 25 mg (0.069 mmol) of the 3-thiophenoxy-5-pentafluorosulfanyl phthalonitrile obtained in Example 7 and 3.1 mg (0.023 mmol) of zinc chloride, and heated to 230° C. After the heating for 3 hours, the solution was cooled to room temperature and purified by silica-gel column chromatography (Hex/AcOEt=8/2), whereby 14 mg of the product of interest was obtained (with a yield of 41%).

$^1$H NMR (300 MHz, CDCl$_3$): δ=7.50 to 7.77 (m, 20H), 7.87 (br, 8H)

$^{19}$F NMR (282 MHz, CDCl$_3$): δ=−146.4 to −147.5 (m, 4F), −165.8 to −166.6 (m, 16F)

MALDI-TOF calculated for $C_{56}H_{28}F_{20}N_8S_8Zn$ [M-H$^+$]$^−$ 1511.92. found 1511.54.

Figure 3:
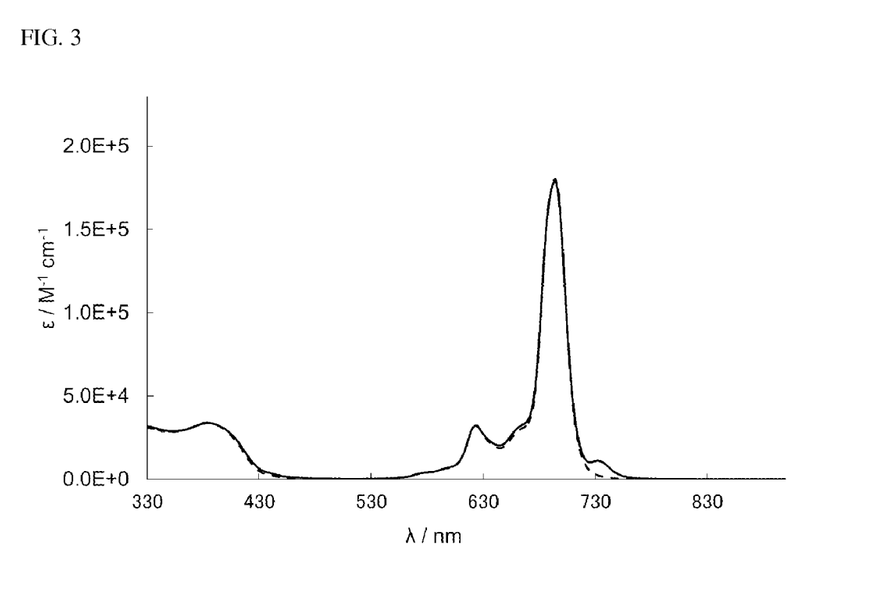
FIG. 3 is the UV/Vis spectrum of the phthalocyanine derivative obtained in Example 10.
Figure 4:
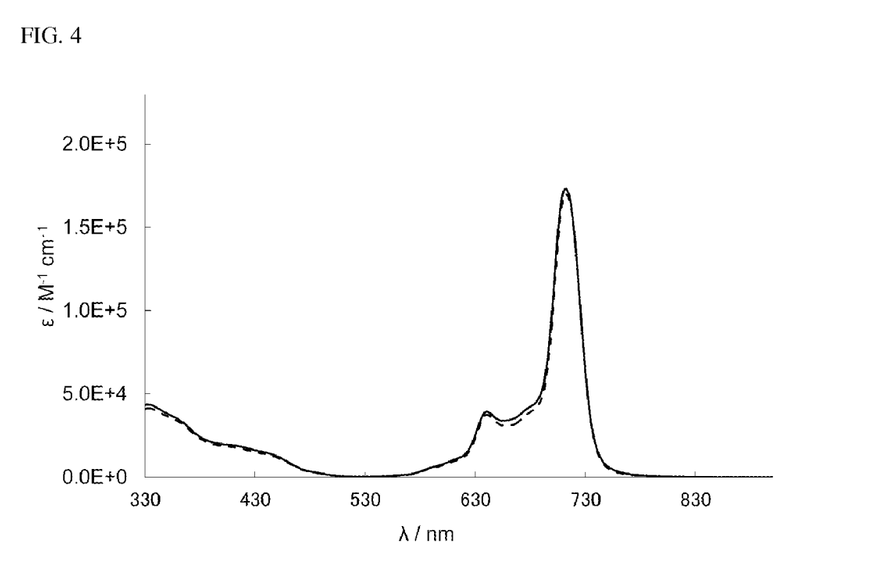
FIG. 4 is the UV/Vis spectrum of the phthalocyanine derivative obtained in Example 11.
Figure 5:
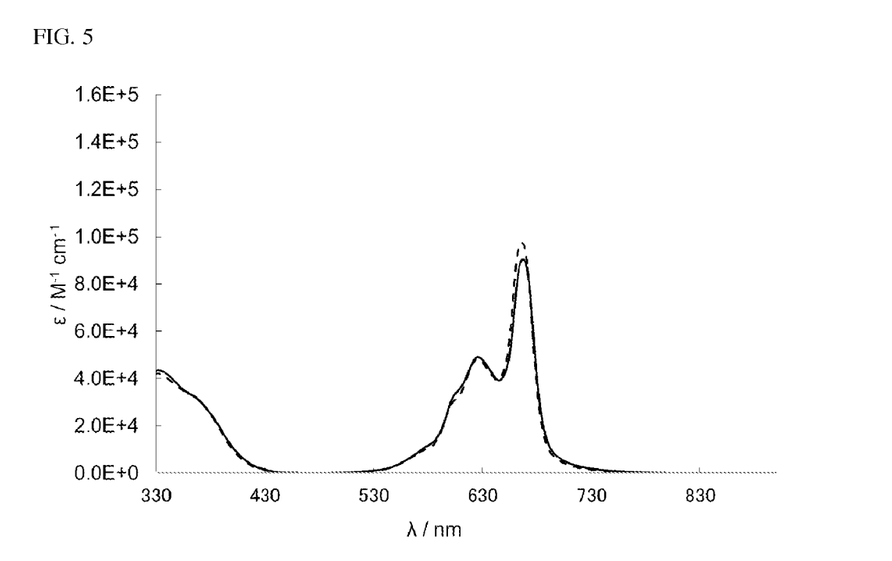
FIG. 5 is the UV/Vis spectrum of a phthalocyanine derivative for comparison.
Figure 6:
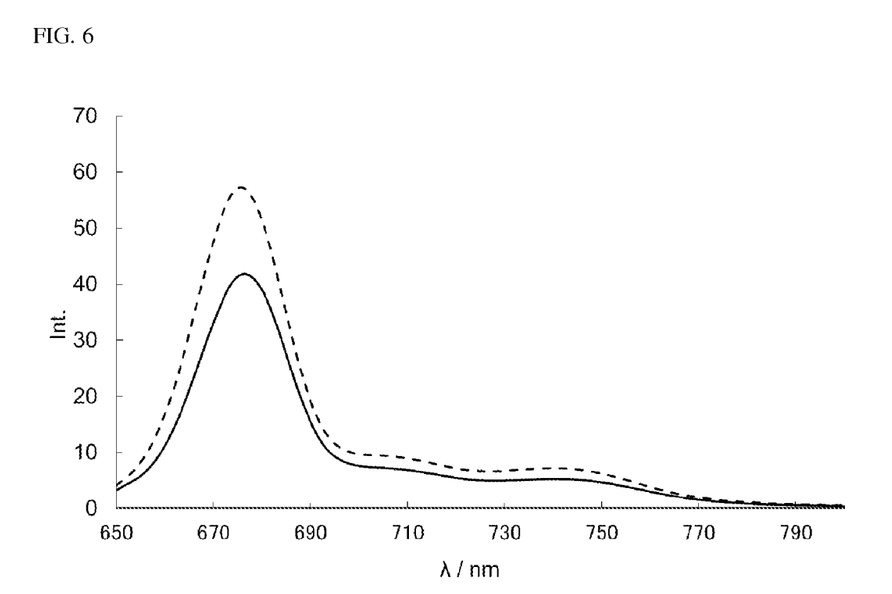
FIG. 6 is the fluorescence spectrum of the phthalocyanine derivative obtained in Example 8.
Figure 7:
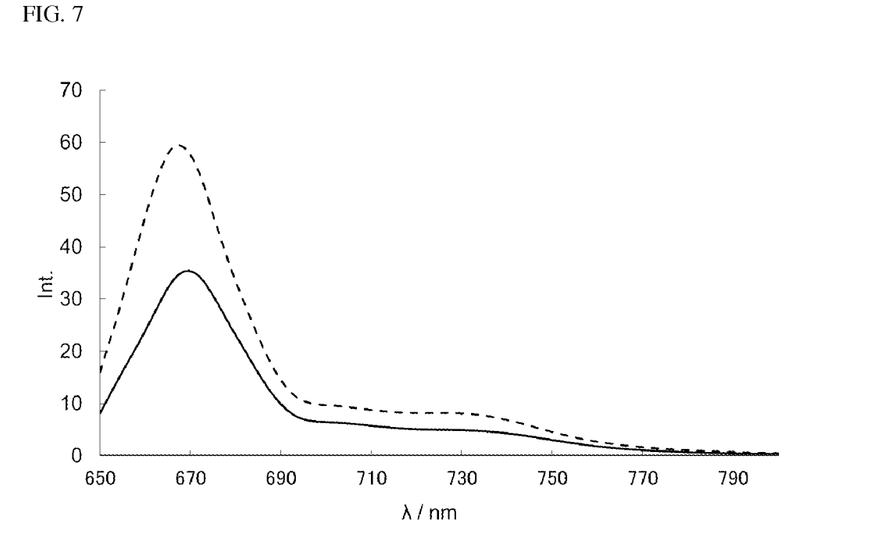
FIG. 7 is the fluorescence spectrum of the phthalocyanine derivative obtained in Example 9.
Figure 8:
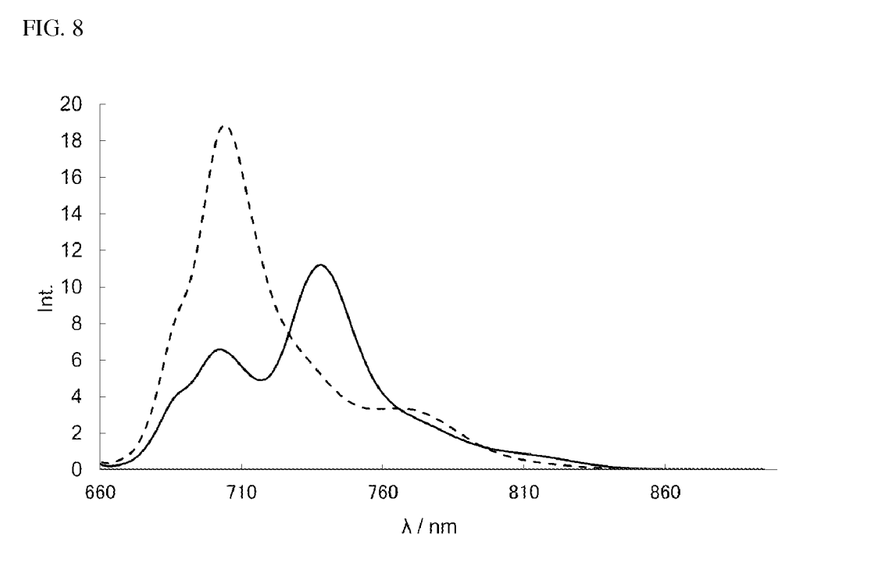
FIG. 8 is the fluorescence spectrum of the phthalocyanine derivative obtained in Example 10.
Figure 9:
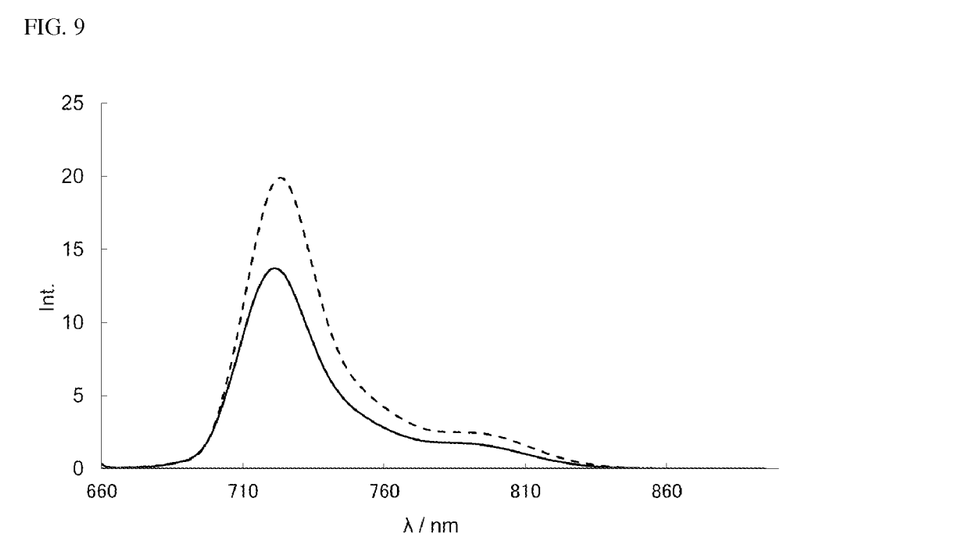
FIG. 9 is the fluorescence spectrum of the phthalocyanine derivative obtained in Example 11.

FIGS. 1 to 4 show the UV/Vis spectra of the inventive phthalocyanine derivatives obtained above in Examples 8 to 11 in methylene chloride. For the purpose of comparison, FIG. 5 shows the UV/Vis spectrum of the trifluoromethyl phthalocyanine disclosed in Patent Literature 1 in methylene chloride. The values of wavelength and molar absorption coefficient for respective peaks are shown in Table 1.

TABLE 1

| Ex. | Compound | λ/nm (ε/M$^{-1}$ cm$^{-1}$) | | | | |
|---|---|---|---|---|---|---|
| 8 | SF5Pc 1.0 × 10$^{-4}$ M (solid line) | 334 (4.13) | 365 (3.39) | 607 (4.38) | 637 (4.50) | 672 (4.96) |
|  | SF5Pc 1.0 × 10$^{-4}$ M + Py (broken line) | 333 (4.13) | 363 (3.41) | 607 (4.36) | 639 (4.48) | 671 (4.97) |
| 9 | CF3-SF5-Pc 1.0 × 10$^{-4}$ M (solid line) | 330 (4.53) | 380 (4.56) | 598 (4.43) | 629 (4.41) | 662 (5.17) |
|  | CF3-SF5-Pc 1.0 × 10$^{-4}$ M + Py (broken line) | 332 (4.49) | 380 (4.53) | 597 (4.39) | 628 (4.37) | 659 (5.17) |
| 10 | OPh-SF5-Pc 1.0 × 10$^{-4}$ M (solid line) | 326 (4.51) | 384 (4.53) | 624 (4.51) | 694 (5.25) | 733 (4.05) |
|  | OPh-SF5-Pc 1.0 × 10$^{-4}$ M + Py (broken line) | 328 (4.50) | 384 (4.53) | 624 (4.51) | 694 (5.26) |  |
| 11 | SPh-SF5-Pc 1.0 × 10$^{-4}$ M (solid line) | 333 (4.64) |  | 407 (4.29) | 641 (4.60) | 712 (5.24) |
|  | SPh-SF5-Pc 1.0 × 10$^{-4}$ M + Py (broken line) | 334 (4.62) |  | 406 (4.27) | 641 (4.58) | 713 (5.23) |
| Com. Ex. | CF3Pc 1.0 × 10$^{-4}$ M (solid line) | 334 (4.64) |  |  | 626 (4.69) | 668 (4.96) |
|  | CF3Pc 1.0 × 10$^{-4}$ M + Py (broken line) | 334 (4.62) | 371 (4.48) | 604 (4.49) | 628 (4.68) | 669 (4.98) |

Figure 1:
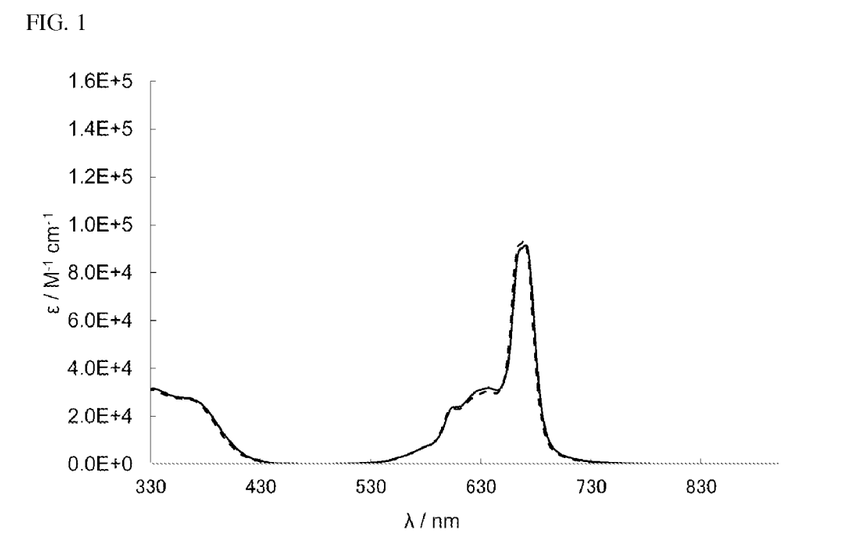
FIG. 1 is the UV/Vis spectrum of the phthalocyanine derivative obtained in Example 8.

The pentafluorosulfanyl phthalocyanine (Example 8) showed almost the same spectrum as the trifluoromethyl phthalocyanine (comparative example)—this result revealed that pentafluorosulfanyl groups have superior coagulation inhibitory effect. However, the trifluoromethyl phthalocyanine (comparative example) was too poorly soluble in an organic solvent to be purified by column chromatography, whereas the pentafluorosulfanyl phthalocyanine obtained in Example 8 was capable of dissolving to a high concentration in an organic solvent, so that it was easy to purify. In other words, the introduction of pentafluorosulfanyl groups succeeded in an improvement in solubility which was not achieved with trifluoromethyl groups.

Figure 2:
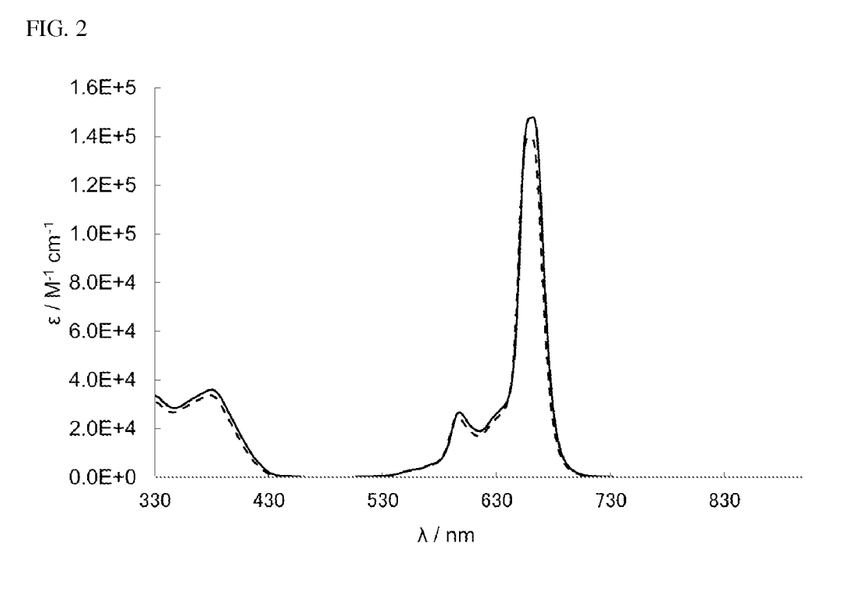
FIG. 2 is the UV/Vis spectrum of the phthalocyanine derivative obtained in Example 9.

It was also found that the trifluoromethyl-pentafluorosulfanyl phthalocyanine obtained in Example 9 is superior in solubility and suppression of coagulation to the phthalocyanine obtained in Example 8. These effects are believed to be attributable to the bulkiness of substituents, high lipid solubility of fluorine atoms, and electrostatic repulsion between fluorine atoms.

As for the phthalocyanine derivatives of Examples 10 and 11 having phenoxy or thiophenoxy groups introduced thereinto, the peak in the Q band showed a significant redshift. Particularly in the case of the phthalocyanine derivative having phenoxy groups introduced thereinto, there appeared a small peak in the vicinity of 730 nm, but the peaks were merged back into one by addition of pyridine; thus, this is believed to be due to protonation. Since UV/Vis spectra of phthalocyanines are greatly affected by their substituent at the zα-position, it is believed that also in the case of the present invention, the spectra were greatly affected by the effects of an electron-donating group introduced into the α-position of the phthalocyanines.

Figure 10:
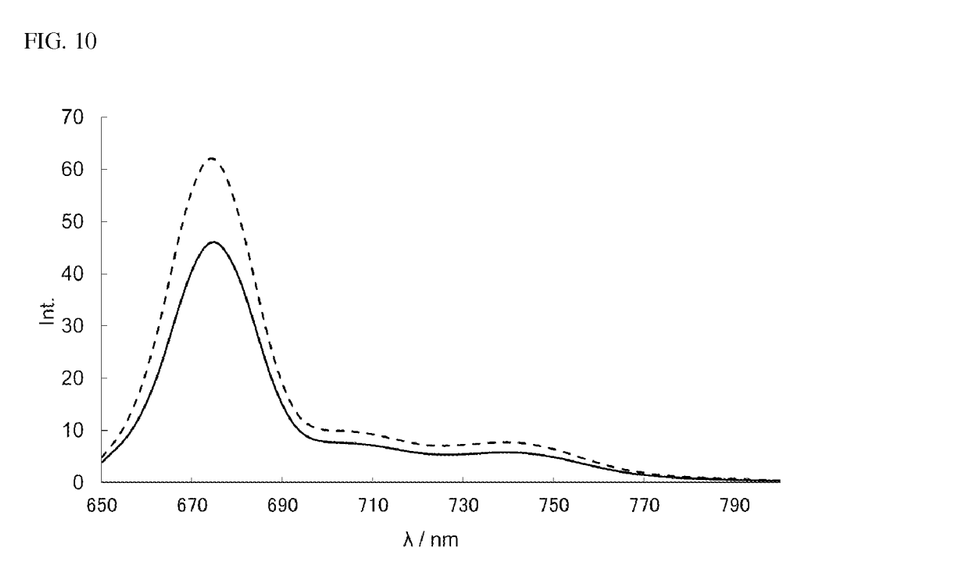
FIG. 10 is the fluorescence spectrum of a phthalocyanine derivative for comparison.

FIGS. 6 to 9 show the fluorescence spectra of the inventive phthalocyanine derivatives obtained above in Examples 8 to 11 in methylene chloride. For the purpose of comparison, FIG. 10 shows the fluorescence spectrum of the trifluoromethyl phthalocyanine disclosed in Patent Literature 1 in methylene chloride. The values of wavelength and fluorescence quantum yield for respective peaks are shown in Table 2.

TABLE 2

| Ex. | Compound | $\lambda_{em}$ (nm) | $\Phi_f$ |
|---|---|---|---|
| 8 | SF5Pc CH2C12 (solid line) | 676 | 0.55 |
|  | SF5Pc CH2C12—Py (broken line) | 676 | 0.74 |
| 9 | CF3—SF5Pc CH2C12 (solid line) | 669 | 0.52 |
|  | CF3—SF5Pc CH2C12—Py (broken line) | 667 | 0.84 |
| 10 | OPh—SF5Pc CH2C12 (solid line) | 738 | 0.26 |
|  | OPh—SF5Pc CH2C12—Py (broken line) | 704 | 0.34 |
| 11 | SPh—SF5Pc CH2C12 (solid line) | 721 | 0.24 |
|  | SPh—SF5Pc CH2C12—Py (broken line) | 723 | 0.34 |
| Com. Ex. | CF3Pc CH2C12 (solid line) | 675 | 0.58 |
|  | CF3Pc CH2C12—Py (broken line) | 674 | 0.76 |

The phthalocyanine derivatives having fluorine introduced thereinto have a relatively high fluorescence quantum yield. In particular, the trifluoromethyl-pentafluorosulfanyl phthalocyanine of Example 9 shows a very high fluorescence quantum yield as high as 0.84 in the presence of pyridine. This tendency is common to those phthalocyanines bearing fluorine-containing functional groups and thus is presumed to be attributable to the effects of fluorine. On the other hand, the phthalocyanine derivatives of Examples 10 and 11, which contain pentafluorosulfanyl groups as electron-accepting groups and phenoxy or thiophenoxy groups as electron-donating groups, tend to show a decrease in fluorescence quantum yield. This is believed to be due to electron transfer between the electron-donating groups and the electron-accepting groups. These two phthalocyanine derivatives both showed moderate values, and not zero values, for fluorescence quantum yield—this is considered to be because there existed asymmetric isomers of these derivatives so that the flow of electrons was not fixed in a certain direction.

What is claimed is:

1. A phthalocyanine derivative of the following general formula (1):

[Formula 1]

(wherein M is a hydrogen atom, a metal element, a metalloid element, a metal oxide, a metalloid oxide, a metal hydroxide, a metalloid hydroxide, a metal halide, or a metalloid halide, and R is each independently a hydrogen atom, an alkyloxy group, an aryloxy group, an alkyl sulfide group, an aryl sulfide group, or a trifluoromethyl group).

2. The phthalocyanine derivative according to claim 1, wherein R is a hydrogen atom.

3. The phthalocyanine derivative according to claim 1, wherein R is an alkyloxy group, an aryloxy group, an alkyl sulfide group, an aryl sulfide group, or a trifluoromethyl group.

4. The phthalocyanine derivative according to claim 1, wherein R is a trifluoromethyl group, a phenoxy group, or a phenyl sulfide group.

5. A halogen-containing pentafluorosulfanyl benzene derivative of the following general formula (2):

[Formula 2]

(wherein Hal is a halogen atom, and X is a hydrogen atom, a halogen atom, or a cyano group).

6. A pentafluorosulfanyl phthalonitrile derivative of the following general formula (3):

[Formula 3]

(3)

(wherein R is a hydrogen atom, an alkyloxy group, an aryloxy group, an alkyl sulfide group, an aryl sulfide group, or a trifluoromethyl group).

7. A process for preparing the phthalocyanine derivative according to claim 1, the process comprising the steps of:
   (A) providing a pentafluorosulfanyl phthalonitrile derivative of the following general formula (3):

[Formula 4]

(3)

(wherein R is a hydrogen atom, an alkyloxy group, an aryloxy group, an alkyl sulfide group, an aryl sulfide group, or a trifluoromethyl group); and
   (B) heating the pentafluorosulfanyl phthalonitrile derivative together with hydrogen, a metal, a metalloid, a metal oxide, a metalloid oxide, a metal hydroxide, a metalloid hydroxide, a metal halide, or a metalloid halide.

8. The process according to claim 7, wherein R in the pentafluorosulfanyl phthalonitrile derivative of the general formula (3) is selected from the group consisting of a hydrogen atom, an alkyl sulfide group, an aryl sulfide group, and a trifluoromethyl group;
   wherein the step (A) is a step of providing the pentafluorosulfanyl phthalonitrile derivative of the general formula (3), by following a step of converting a halogen-containing pentafluorosulfanyl benzene derivative of the following general formula (2):

[Formula 5]

(2)

(wherein Hal is a halogen atom, and X is a hydrogen atom, a halogen atom, or a cyano group) into the pentafluorosulfanyl phthalonitrile derivative the general formula (3), wherein when X is H, Hal in the derivative of general formula (2) is converted into CN group by a cyanide;
when X is CN, Hal in the derivative of general formula (2) is converted into a trifluoromethyl group by the Yagupolskii reagent, and to an aryloxy group by phenols, or to an arylsulfide group by thiophenols; and
when X is Hal, one of Hal in the derivative of general formula (2) is converted into CN by cyanide and the other Hal in the derivative of general formula (2) is converted into a trifluoromethyl group by the Yagupolskii reagent, and to an aryloxy group by phenols, or to an arylsulfide group by thiophenols.

9. A process for preparing the phthalocyanine derivative according to claim 2, the process comprising the steps of:
   (A1) converting Hal in a halogen-containing pentafluorosulfanyl benzene derivative of the following general formula (2a):

[Formula 6]

(2a)

(wherein Hal is a halogen atom)
into a cyano group, to thereby provide a pentafluorosulfanyl phthalonitrile derivative of the following general formula (3a):

[Formula 7]

(3a)

and
   (B) heating the pentafluorosulfanyl phthalonitrile derivative together with hydrogen, a metal, a metalloid, a metal oxide, a metalloid oxide, a metal hydroxide, a metalloid hydroxide, a metal halide, or a metalloid halide.

10. A process for preparing the phthalocyanine derivative according to claim 3, the process comprising the steps of:
   (A2) converting one Hal and the other Hal in a halogen-containing pentafluorosulfanyl benzene derivative of the following general formula (2b):

[Formula 8]

(2b)

(wherein Hal is a halogen atom)
into a cyano group and R', respectively, to thereby provide a pentafluorosulfanyl phthalonitrile derivative of the following general formula (3b):

[Formula 9]

(3b)

(wherein R' is alkyloxy group, an aryloxy group, an alkyl sulfide group, an aryl sulfide group, or a trifluoromethyl group); and (B) heating the pentafluorosulfanyl phthalonitrile derivative together with hydrogen, a metal, a metalloid, a metal oxide, a metalloid oxide, a metal hydroxide, a metalloid hydroxide, a metal halide, or a metalloid halide.

11. A process for preparing the phthalocyanine derivative according to claim 3, the process comprising the steps of:

(A3) converting Hal in a halogen-containing pentafluorosulfanyl benzene derivative of the following general formula (2c):

[Formula 10]

(2c)

(wherein Hal is a halogen atom)

into R', to thereby provide a pentafluorosulfanyl phthalonitrile derivative of the following general formula (3c):

[Formula 11]

(3c)

(wherein R' is an alkyloxy group, an aryloxy group, an alkyl sulfide group, an aryl sulfide group, or a trifluoromethyl group); and (B) heating the pentafluorosulfanyl phthalonitrile derivative together with hydrogen, a metal, a metalloid, a metal oxide, a metalloid oxide, a metal hydroxide, a metalloid hydroxide, a metal halide, or a metalloid halide.

* * * * *